(12) United States Patent
Duccini et al.

(10) Patent No.: US 10,772,826 B2
(45) Date of Patent: Sep. 15, 2020

(54) CONTROLLED RELEASE OF ACTIVE SUBSTANCES

(71) Applicant: Societe d'Exploitation de Produits Pour les Industries Chimiques Seppic, Paris (FR)

(72) Inventors: Yves Duccini, Vielmur/agout (FR); Gérard Trouve, Castres (FR)

(73) Assignee: SOCIETE D'EXPLOITATION DE PRODUITS POUR LES INDUSTRIES CHIMIQUES SEPPIC, Paris (FR)

( * ) Notice: Subject to any disclaimer, the term of this patent is extended or adjusted under 35 U.S.C. 154(b) by 0 days.

(21) Appl. No.: 15/536,432

(22) PCT Filed: Dec. 7, 2015

(86) PCT No.: PCT/FR2015/053345
§ 371 (c)(1),
(2) Date: Jun. 15, 2017

(87) PCT Pub. No.: WO2016/097525
PCT Pub. Date: Jun. 23, 2016

(65) Prior Publication Data
US 2017/0348223 A1    Dec. 7, 2017

(30) Foreign Application Priority Data
Dec. 15, 2014  (FR) ..................................... 14 62413

(51) Int. Cl.
*A61K 9/00* (2006.01)
*A61K 9/16* (2006.01)
*A61K 31/045* (2006.01)
*A61K 31/20* (2006.01)
*A61K 31/7024* (2006.01)

(52) U.S. Cl.
CPC .......... *A61K 9/0002* (2013.01); *A61K 9/0053* (2013.01); *A61K 9/1611* (2013.01); *A61K 9/1617* (2013.01); *A61K 9/1623* (2013.01); *A61K 9/1664* (2013.01); *A61K 31/045* (2013.01); *A61K 31/20* (2013.01); *A61K 31/7024* (2013.01)

(58) Field of Classification Search
None
See application file for complete search history.

(56) References Cited

FOREIGN PATENT DOCUMENTS

WO    WO-2007018943 A2 *  2/2007  ........... A61K 9/1676

\* cited by examiner

*Primary Examiner* — Dennis J Parad
(74) *Attorney, Agent, or Firm* — Nixon & Vanderhye

(57) ABSTRACT

A water-insoluble composition, solid in appearance at a temperature of less than or equal to 20° C., comprising, for 100% of the mass of same: —X1% by mass of at least one lipophilic surfactant having a value HLB, H1, greater than or equal to 1 and less than 10; —X2% by mass of at least one hydrophilic surfactant having a value HLB, H2, greater than or equal to 10 and less than or equal to 20; characterised by the fact that the HLB of same=X1.H1+X2.H2, X1 and X2 varying from 2 to 60, and characterised in that it is free of acrylic polymer and/or of acetate succinate.

14 Claims, 5 Drawing Sheets

CONTROLLED RELEASE OF ACTIVE SUBSTANCES

Figure 1:
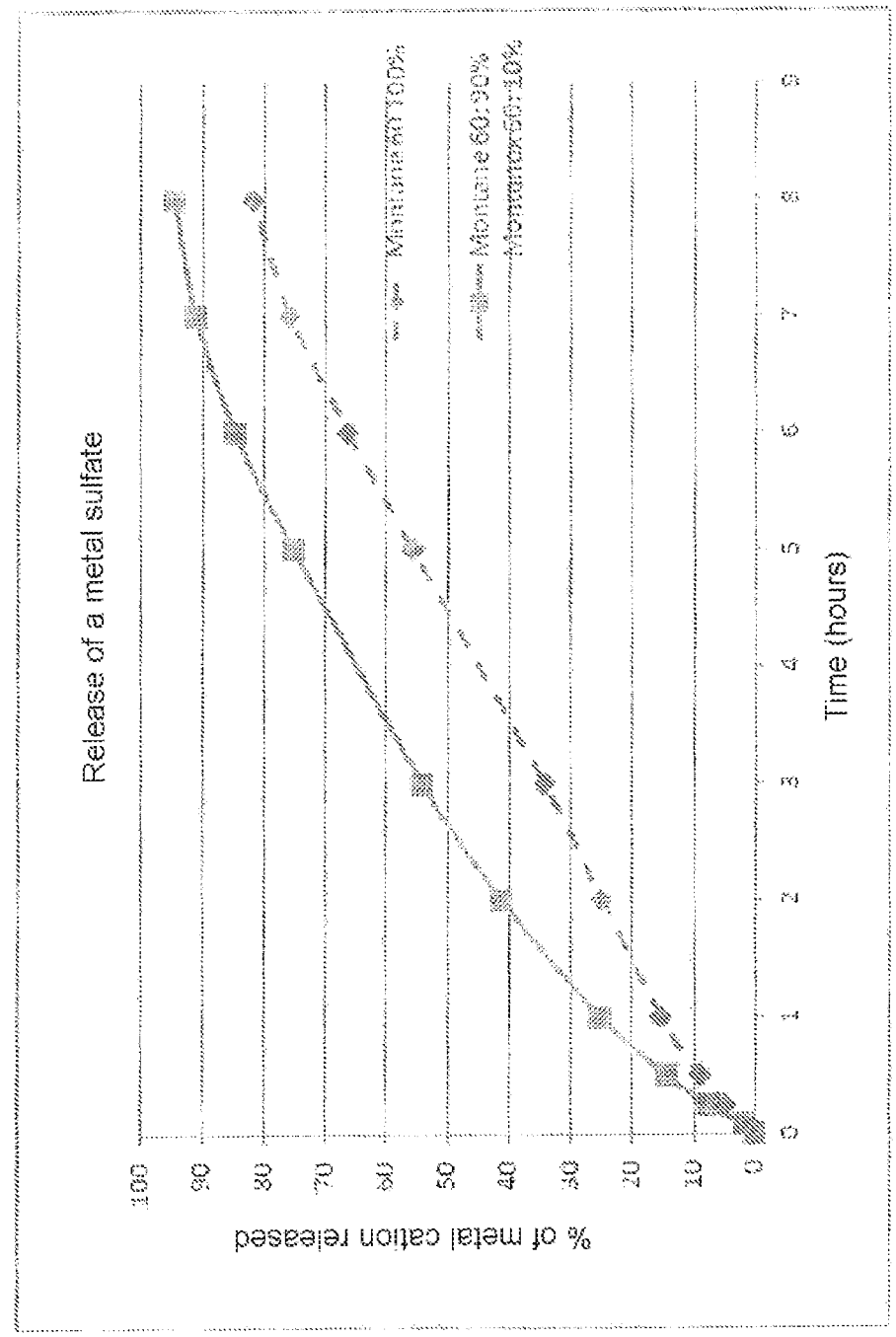

The present invention relates to the release of pharmaceutical, food or veterinary active principles in the human or animal body according to fully controlled kinetics and with masking of unpleasant tastes by prilling or hot melt coating technology.

The pharmaceutical industry, the food supplements industry and the veterinary products industry employ formulations having increasingly complex molecules, often with an unpleasant taste, sometimes fragile, and which must diffuse in the organisms following quite particular kinetics.

In fact, to provide the intended nutritional or therapeutic advantages, the molecules introduced in soft capsules, hard capsules, tablets or even in food must not dissolve at the same rate and in the same environment.

In particular, the molecules are destroyed when they circulate in the human stomach or in the animal stomach. Its very acid pH and the presence of digestive juices and enzymes mean that few molecules remain intact after passage through this organ, which will take one to two hours in humans and much longer in ruminants.

Moreover, taking medicine or a food supplement is often associated with ingestion of food (almost always in the case of animals), which further increases the chemical reactions that may degrade certain molecules.

Conversely, rapid release of some if not all of the active substance is sometimes required so as to obtain an almost immediate effect. This applies for example to antiemetics, analgesics or nonsteroidal anti-inflammatories.

In certain cases it is desirable to endow the molecule introduced with a so-called gastro-resistant property. It is then desirable that the active molecule is only released after passing through the stomach; this is the case with molecules that are often fragile and act on the digestion, such as antioxidants, antibacterials, strains for regenerating the intestinal flora (prebiotics) and those facilitating its growth (probiotics), certain antibiotics and anti-inflammatories. Often a person skilled in the art even wishes to control precisely where in the intestine the active molecule will be released. The intestine is very long and the transit time may be considerable.

For ruminants, estimates are between four and five hours in the small intestine and from forty to sixty hours in the large intestine. To control at what rate and therefore at what place in the intestine the active molecule will be released is very difficult, but is very beneficial for the efficacy of the drug.

Moreover, many molecules used in pharmacy, food supplements or veterinary products have an unpleasant, bitter or astringent taste. A person skilled in the art will wish to mask these tastes while controlling the kinetics of diffusion in the organism, as described above.

Besides the examples of medicinal products described above, the decline in food quality is leading the food supplements companies and even food industry companies to supplement their products with substances that humans or animals lack. Many substances, when used in the pure state, have an unpleasant taste or are too fragile to survive passage through the stomach or the food manufacturing processes (cooking, pasteurization, spraying, etc.).

We may mention once again probiotics and prebiotics, but also antioxidants, vitamins, mineral salts, and certain amino acids.

Numerous solutions of encapsulation, absorption or film coating have been developed by industry to solve the problems described above.

None is entirely satisfactory and in particular none solves both the problems of taste and of very precise release in the digestive system.

Among these solutions we may mention: absorption on porous supports such as silicas, celluloses, polymethacrylates or polyacrylates.

The major drawbacks of absorption on porous supports are:
the small amount of active substance absorbed,
the granulometries of the supports, making their use perceptible by the consumer,
the impossibility of absorbing certain active substances,
it is almost impossible to control release, which generally takes place by "exchange" between the product absorbed and the medium surrounding it.

We should add that the taste is often still perceptible.

Film coating of the active substances with solutions of sugars or polymers by "pan coating" techniques is by far the most used technique in the pharmaceutical industry for masking taste and notably for making gastro-resistant tablets.

The technique consisting of coating solid cores with wax films (or "hot melt coating") is also known. We may cite for example the patents of the company Balchem: WO 2004/060074 A1 or U.S. Pat. No. 6,835,397. The technique described in these patents employs self-emulsifiable products as film-forming excipients. Moreover, it is not possible to control the release of active substances precisely, and the technique requires the active substance to be exposed to considerable heat for several minutes, which may cause its degradation. Finally, combination with a taste masking effect is not described.

This technique does not make it possible to control the rate of release other than by adjusting the amount of wax deposited on the core, which may become problematic if release over long periods of time is desired, since the rate of release is inversely proportional to the amount of wax deposited.

Finally, "prilling" is a technology for forming microbeads consisting of an active principle dispersed in a wax. It is described in some articles and patents, but generally this technology is carried out using commercially available waxes and does not make it possible to control the dissolution rate in the organism. It only serves for masking taste, and delayed release is claimed, without being more precise.

As an example, we may mention patent CN 101513392, which lists numerous excipients that can be used, but does not claim to regulate the rate of release.

Accordingly, the invention relates to a water-insoluble composition, of solid appearance at a temperature less than or equal to 20° C., comprising for 100% of its weight:
X1 wt % of at least one lipophilic surfactant having an HLB value, H1, greater than or equal to 1 and below 10;
X2 wt % of at least one hydrophilic surfactant having an HLB value, H2, greater than or equal to 10 and less than or equal to 20;
characterized in that its HLB=X1.H1+X2.H2, X1 and X2 varying from 2 to 60, and characterized in that it is free from acrylic polymer and/or succinate acetate.

Moreover, according to other embodiments, the invention also relates to:

a composition as defined above, characterized in that H1 is greater than or equal to 3.4 and less than or equal to 6 and H2 is greater than or equal to 14 and less than or equal to 16;

a composition as defined above, characterized in that it comprises from two to five surfactants each having an HLB, Hi, and a proportion by weight Xi such that the HLB value of said composition is equal to ΣXi.Hi, with i between 2 and 5, Xi between 2% and 60% and ΣXi≤100%.

a composition as defined above, characterized in that said at least one hydrophilic surfactant is selected from ethoxylated sorbitan esters, ethoxylated alcohols or acids, polyglycerol esters, glucose ethers, and block copolymers of ethylene oxide and propylene oxide;

a composition as defined above, characterized in that said at least one lipophilic surfactant is selected from:

esters of fatty acids and sugars; said fatty acids being selected from stearic, palmitic, ketostearic, arachidic, and behenic acids; said sugars being for example glucose, sorbitol, mannitose, mannitol, sucrose, mannose, xylitol or xylose;

esters of fatty acids and glycerol, said fatty acids being selected from stearic, palmitic, ketostearic, arachidic, and behenic acids;

ethers of fatty alcohols and sugars, the fatty alcohols being stearic, palmitic, ketostearic, arachidic, and behenic alcohols; said sugars being for example reducing sugars, and more particularly glucose, xylose, arabinose, mannose, or sucrose;

divalent salts of fatty acids such as the magnesium, zinc or calcium salts of stearic, palmitic, ketostearic, arachidic, and behenic acids;

fatty alcohols condensed with propylene oxide and/or butylene oxide;

block copolymers of alkoxides (ethylene, propylene, butylene, etc.), rich in propylene oxide or butylene oxide.

A composition as defined above, characterized in that said at least one lipophilic surfactant is a sorbitan stearate.

A composition as defined above, characterized in that it further comprises, to 100% of its weight, an amount of additives such as a perfume, a flavoring, a palatabilizer, a dye, a pigment, or a solid diluent at a temperature less than or equal to 20° C. such as a hydrogenated vegetable oil such as soybean oil, castor oil, colza oil or hydrogenated palm oil, shea butter, a wax such as beeswax or carnauba wax.

The present invention also relates to:

a controlled-release galenical formulation comprising for 100% of its weight:

from 20 to 95 wt % of at least one pharmaceutical, food or veterinary active substance; and from 5 to 80 wt % of a composition as defined above.

a formulation as defined above, characterized in that it comprises for 100% of its weight:

from 50 to 90 wt % of at least one pharmaceutical, food or veterinary active substance; and from 10 to 50 wt % of a composition as defined above.

a formulation as defined above, characterized in that the active substance is selected from the antiulcer drugs, antidiabetic drugs, anticoagulants, antithrombotic agents, hypolipemic drugs, antiarhythmic drugs, vasodilators, antiangina drugs, antihypertensives, vasoprotective agents, antibiotics, antifungals, antivirals, anticancer drugs, anti-inflammatories, analgesics, antiepileptics, antiparkinsonian drugs, neuroleptics, hypnotics, anxiolytics, psychostimulants, antimigraine drugs, antidepressants, antitussives, antihistamines or antiallergic drugs.

a formulation as defined above, characterized in that the active substance is selected from the following compounds: metformin, acetylsalicylic acid, pentoxifylline, prazosin, acyclovir, nifedipine, diltiazem, naproxen, ibuprofen, flurbiprofen, ketoprofen, fenoprofen, indomethacin, diclofenac, fentiazac, estradiol valerate, metoprolol, sulpiride, captopril, cimetidine, zidovudine, nicardipine, terfenadine, atenolol, salbutamol, carbamazepine, ranitidine, enalapril, simvastatin, fluoxetine, alprazolam, famotidine, ganciclovir, famciclovir, spironolactone, 5-ASA, quinidine, morphine, pentazocine, paracetamol, omeprazole, metoclopramide and mixtures thereof.

a formulation as defined above, characterized in that the active substance is selected from a list of nutraceuticals: tonics, antioxidants, and stimulants such as mineral salts notably iron salts, vitamins, urea, caffeine.

The present invention also relates to the use of a composition as defined above, for encapsulation of a pharmaceutical, food or veterinary active substance in a controlled-release galenical formulation.

Finally, the present invention relates to a method for preparing a formulation as defined above, comprising the following steps:

a) heating a composition as defined above to a temperature greater than or equal to 40° C. in order to melt said composition;

b) mixing the pharmaceutical, food or veterinary active substance in the molten composition resulting from step a);

c) cooling the mixture in order to obtain encapsulation or coating of said active substance;

characterized in that the HLB values of the surfactants and their proportions by weight in the composition introduced in step a) are selected as a function of the targeted duration of the subsequent release of said active substance.

"Waxy composition" means a composition that is insoluble in water or of low solubility in water and is solid at room temperature (i.e. 20° C.).

The choice of the weight ratio of the two types of surfactants makes it possible to control the dissolution rate of the waxy film deposited on a core in the case when "hot melt coating" is used, or the dissolution rate of the microbead formed by "prilling". The rate of release of the active principles contained in the cores or in the microbeads is directly linked to the dissolution rates of the waxy films or microbeads obtained by these techniques.

The advantage of the composition according to the present invention is very precise control of the rates of release of an active molecule in the human or animal digestive system, while masking the taste of said molecule. It is even possible to obtain a delaying effect, giving zero release during gastric transit, only beginning to release the active substance in the intestine. It will be possible to "modulate" this release as a function of the target site in the intestine.

This "fine" control of the release of the active substance in the digestive system is achieved owing to a mixture of several surfactants that are solid at room temperature and are selected as a function of their respective HLB values. The hydrophilic surfactants are characterized by an HLB value greater than or equal to 10. The lipophilic surfactants have an HLB value greater than or equal to 1 and below 10.

The waxy compositions according to the invention generally comprise a minimum of two surfactants, but the compositions may incorporate several different surfactants.

It is the mixture of these surfactants, varying both their compositions to obtain mixtures with quite precise HLB values and their proportions in the mixture, that will allow very fine control of the release of the chosen active substance while preserving the taste masking properties.

According to a particular embodiment of the invention, the property of gastro-resistance is not obtained, as in most publications, by using acrylic polymers or succinate acetates, but by the judicious choice of surfactants having an HLB value that varies with the pH.

Among the lipophilic surfactants that are usable, we may mention:

the esters of fatty acids that are solid at room temperature, and of sugars; said fatty acids being selected from stearic, palmitic, ketostearic, arachidic, and behenic acids; said sugars being for example glucose, sorbitol, mannitose, mannitol, sucrose, mannose, xylitol or xylose.

We may mention more particularly the ester of sorbitol and palmitic acid marketed under the brand name Montane™40, the esters of sorbitol and stearic acid marketed under the brand names Montane™60 and Montane™65. The esters of fatty acids and glycerol, said fatty acids being selected from stearic, palmitic, ketostearic, arachidic, and behenic acids.

The ethers of fatty alcohol and sugars. The fatty alcohols that are particularly useful being the stearic, palmitic, ketostearic, arachidic, and behenic alcohols; said sugars being for example reducing sugars, and more particularly glucose, xylose, arabinose, mannose, or sucrose The divalent salts of fatty acids such as the magnesium, zinc or calcium salts of stearic, palmitic, ketostearic, arachidic, and behenic acids.

The fatty alcohols that are solid at room temperature (20° C.), condensed with propylene oxide and/or butylene oxide.

The block copolymers of alkoxides (ethylene, propylene, butylene, etc.), rich in propylene oxide and/or butylene oxide.

Among the hydrophilic surfactants that are usable, there are:

the ethoxylated derivatives of the compounds mentioned above having a number of ethylene oxide units greater than or equal to five, preferably greater than ten, preferably equal to twenty. We may mention more particularly the ethoxylated derivatives having a number of ethylene oxide units greater than or equal to five, preferably greater than or equal to ten, preferably equal to twenty, of the esters of fatty acids that are solid at room temperature and of sugars; said fatty acids being selected from stearic, palmitic, ketostearic, arachidic, and behenic acids; said sugars being for example sorbitol, mannitol or xylitol. We may mention even more particularly the esters of stearic acid and ethoxylated sorbitol with 20 moles of ethylene oxide and marketed under the brand names Montanox™60 and Montanox™65, the esters of palmitic acid and ethoxylated sorbitol with 20 moles of ethylene oxide and marketed under the brand names Montanox™40, the esters of stearic acid and ethoxylated sorbitol with 20 moles of ethylene oxide and marketed under the brand names Montanox™60 and Montanox™65.

the esters of polyglycerol formed by condensation of a fatty acid, selected from stearic, palmitic, ketostearic, arachidic, and behenic acids, and of a polyglycerol comprising at least three glycerol units.

the alkoxylated fatty alcohols formed by condensation of alcohols that are solid at room temperature and of ethylene oxide and/or propylene oxide, rich in ethylene oxide.

the block copolymers of alkoxides (ethylene, propylene, butylene, etc.), rich in ethylene oxide.

The surfactants whose HLB value varies with the pH may be selected from the following classes:

fatty acids (lipophilic at pH below about 4 and hydrophilic at pH above about 5). The preferred fatty acids are stearic, palmitic, ketostearic, arachidic, and behenic acids.

monovalent sodium and potassium salts of fatty acids such as stearic, palmitic, ketostearic, arachidic, and behenic acids.

surfactants resulting from the N-acylation reaction between a fatty acid chloride or a fatty acid methyl ester or a fatty acid and at least one amino acid or at least one peptide or at least one protein hydrolyzate or at least one protein or at least one peptide hydrolyzate, more particularly the surfactants resulting from the N-acylation reaction between a fatty acid chloride or a fatty acid methyl ester or a fatty acid and at least one amino acid, also called N-acylate of amino acids or lipoamino acids.

The HLB values are additive quantities. A composition consisting of two surfactants with respective HLB values H1 and H2 in respective proportions by weight x1 and x2 will therefore be characterized by a value $HLB_c$ that may be calculated from the formula:

$$HLB_c = x_1 * H_1 + x_2 * H_2$$

The present invention also relates to a method consisting of dispersing, suspending or emulsifying the substance whose taste is to be masked and whose release is to be controlled, in a mixture of molten surfactants and allowing this mixture to fall dropwise through nozzles in a stream of liquid nitrogen or of air cooled with liquid nitrogen. The diameter of the nozzles will be selected so that it is about half of that of the desired microbeads. Thus, nozzles will preferably be selected with a diameter between 50 μm and 1000 μm, preferably between 100 μm and 500 μm.

A variant of this method consists of directing the molten waxy mixture comprising the surfactants and the active substance onto the surface of a disk rotating at a controlled speed; the speed of the disk causes, through centrifugation, the formation of microdroplets that will solidify and give solid microbeads as they fall in a stream of air cold or in liquid nitrogen.

Another way of implementing the invention is to deposit a layer of this mixture of molten surfactants on the active substance by means of a cooling table equipped with dispersing curtains or evaporating nozzles. A film-coating turbine may also be used for this operation.

In both cases, the molten material containing the active substance in suspension (in the case of powder), dissolved (in the case of a hydrophobic liquid) or emulsified (in the case of a hydrophilic liquid), will solidify immediately and coat or encapsulate the active substance. These two technologies will give granules or beads of encapsulated active substance.

These technologies may be improved as follows: by vibrating the nozzles, beads of the same size can be obtained (monodisperse granulometry), which makes their possible use in lozenges or tablets even easier.

However, flavorings may also be incorporated in the mixtures of surfactants, which will make the product more attractive for animals or for young children.

EXAMPLE 1: CONTROLLED RELEASE AND TASTE MASKING OF A HYDROPHILIC METAL Powder In this example, the active substance to be encapsulated is a hydrophilic powder consisting of a metal sulfate. It is used for restoring the metal balance if there is a deficiency, notably in young children.

Its taste is a very astringent taste typical of the metal salts and in particular its hydrophilic character is such that the product dissolves in less than an hour in the stomach, making continuous administration over the day impossible and suddenly increasing the content of metal in the blood.

Said hydrophilic powder for example consists of a calcium, manganese, zinc or iron sulfate.

Description of the Operations:

A 5-ml glass syringe equipped with a 20 G needle for dropping beads of the surfactant/metal powder mixture molten at 75° C. into cold water is used. Then the molten mixture is held in the syringe.

Beads are prepared with a diameter of about 2 mm containing, for 100% of their weight, 50 wt % of hydrophilic powder and 50 wt % of an intimate Montane 60/Montanox 60 mixture in a weight ratio of 90/10.

The release kinetics was evaluated by monitoring the conductivity. A result that meets the requirement is obtained (80 to 100% of active substance released between six hours and eight hours).

Two 30 g samples of beads are prepared, and the following table gives their composition by weight for 100% of their weight.

|  |  |  |
|---|---|---|
| Hydrophilic powder | 50% | 50% |
| Montane 60* | 50% | 45% |
| Montanox 60** |  | 5% |

*Sorbitan monostearate manufactured by SEPPIC
**Ethoxylated sorbitan monostearate with 20 moles of ethylene oxide manufactured by SEPPIC.

Evaluation of the Rate of Release of the Metal Ion:

1 g of beads are dispersed in 100 g of water. The variation of conductivity is monitored as a function of time. The results are illustrated in FIG. 1.

Control: solution with 0.5 g of powder alone in 100 g of water: 3560 mS/cm.

EXAMPLE 2: ENCAPSULATION AND TASTE MASKING OF A VETERINARY ACTIVE SUBSTANCE

In this example the active substance to be protected and encapsulated is a veterinary antiparasitic agent (API). This active principle, administered mainly by the oral route, is very bitter, it is easily detected by felines, whose smell and taste are very sensitive. It is in the form of a white powder of high melting point (135° C.) with very low solubility in water (200 mg/l at 20° C.).

As a veterinary antiparasitic agent, we may mention for example insect repellents for external use: essential oils such as geraniol or lavender extract. Insecticides for internal use: Fiproli, avermectin.

Other examples are anthelmintics and acaricides such as febantel, niclosamide, pyrantel. A very good example is praziquantel.

Encapsulation has the aim of masking the taste of the active principle for about 15 minutes. This means very little release of the API (an amount not exceeding 10 wt % of the API) during this minimum interval of time of 15 minutes, but it must be released completely in a time of one to two hours after administration, in the animal's stomach at pH 4 to 5.

The concentration of active principle in the encapsulating matrix has to approach 40 wt %.

Different mixtures of hydrophilic and lipophilic surfactants were evaluated, combined with 40 wt % of the active substance. The formulations have the following composition, for 100% of their weights:

Active principle: 40%
Lipophilic surfactant: 30%-60%
Hydrophilic surfactant: 0%-30%

| Table of the surfactants used for the tests | | | |
|---|---|---|---|
| Nature | Trade name | HLB | Character |
| Glycerol dibehenate | Compritol 888 (Gattefossé) | 1.8 | lipophilic |
| Glycerol monobehenate | Essai Seppic | 2 | lipophilic |
| Sorbitan stearate | Montane 60 (Seppic) | 4.7 | lipophilic |
| Ethoxylated ketostearyl alcohol (8 EO) | Simulsol 58 PHA (Seppic) | 15.7 | hydrophilic |
| Ethoxylated sorbitan stearate (20 EO) | Montanox 60 (Seppic) | 14.9 | hydrophilic |

Experimental Protocol for Microbead Manufacture

All the utensils used are put in a stove at 100° C. The excipients are melted in the stove at 100° C. The molten excipients are introduced with stirring into a hot 500-mL reactor on a water bath on a magnetic stirrer with thermostatic control at 145° C. The active substance is added and homogenized until an oily liquid of yellowish or brown appearance is obtained. The molten mixture is cooled and then ground and sieved to obtain solid microbeads.

The granulometry of the microbeads is characterized by laser diffraction from their Dv90 (maximum size of 90% of the particles) and their Dv50 (average diameter of the particles), using a MALVERN Mastersizer granulometer.

Experimental Protocol for Release of the Active Substance

The dissolution protocol described in the US pharmacopeia was followed. 100 g of microbeads are dispersed in one liter of aqueous solution at pH 5, maintained at 37° C. Samples are taken periodically and analyzed by HPLC for their concentration of active principle.

| Composition and characterization of the microbeads produced | | | | | | |
|---|---|---|---|---|---|---|
| | Composition by weight | | | | Granulometry | |
| | | | | | (µm) | |
| Reference | Active principle | Lipophilic TA | Hydrophilic TA | HLB microbead | Dv90 | DV50 |
| 1 | 40% | Glycerol dibehenate 60% | 0 | 1.8 | 900 | ND |
| 2 | 40% | Glycerol dibehenate 60% | 0 | 1.8 | 493 | ND |

-continued

Composition and characterization of the microbeads produced

| Reference | Active principle | Lipophilic TA | Hydrophilic TA | HLB microbead | Granulometry (μm) Dv90 | DV50 |
|---|---|---|---|---|---|---|
| 3 | 50% | Glycerol dibehenate 50% | 0 | 1.8 | 872 | ND |
| 4 | 40% | Glycerol dibehenate 50% | Ketostearyl alcohol 8 EO 10% | 4.3 | 494 | 250 |
| 5 | 40% | Glycerol dibehenate 40% | Ketostearyl alcohol 8 EO 20% | 6.6 | 514 | 266 |
| 6 | 40% | Glycerol dibehenate 30% | Ketostearyl alcohol 8 EO 30% | 8.9 | 496 | 248 |
| 7 | 40% | Glycerol monobehenate 60% | 0 | 2 | 555 | 284 |
| 8 | 40% | Glycerol dibehenate 40% | Sorbitan stearate 20 EO 20% | 6.3 | 498 | 252 |

Results for Release of the Active Substance in the Various Tests Performed

Figure 2:
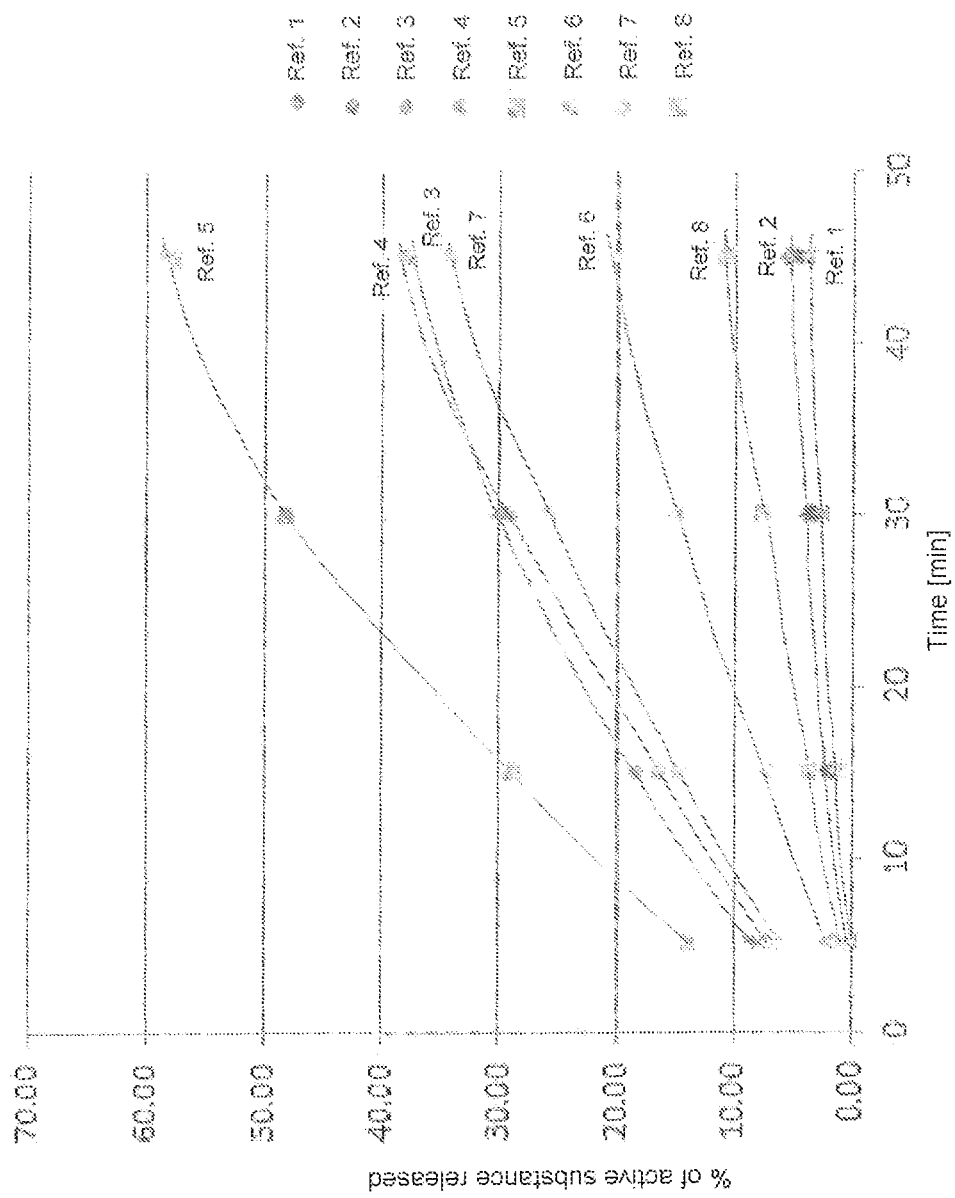

It can be seen from the curves in FIG. 2 that the different compositions tested alter the release profiles of the active principle completely.

Tests 1 and 2, with identical compositions, give release profiles that can be superimposed, showing the reproducibility and robustness of the method. They only allow release of a tiny fraction of the active substance (up to 4 wt % in 30 minutes) and therefore effective taste masking. Test 3 with the same qualitative composition but a higher load of active principle displays a slightly quicker release profile, in accordance with the principles of the laws of diffusion.

The curves also show that the higher the HLB value of the microbead, the quicker the release of the active substance.

The compositions not containing hydrophilic surfactant (and which therefore do not correspond to the invention), such as 7, 1, 2 and 3, effectively release very little active substance in the first quarter of an hour but do not release much more of it thereafter. The active substance therefore remains largely trapped in the capsule and is no longer effective. The composition with the highest HLB value (test 6) releases practically all the active substance in one hour but also a lot of the active substance in fifteen minutes, which means it has limited taste masking properties. It is therefore a question of finding a good compromise, which is the case with compositions such as 4, 5 and 8. The compositions aimed at are those that release less than 10% of active substance in 15 minutes to provide the taste masking effect and more than 30% of active substance in 45 minutes to provide efficacy of the active principle in the alimentary canal.

Figure 3:
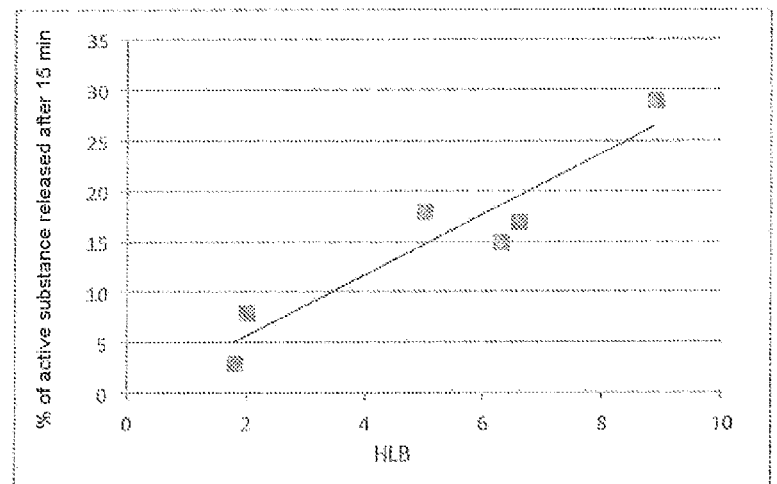

This correlation can also be seen in the graph in FIG. 3, showing the percentage by weight of active substance released after 15 minutes as a function of the HLB value of the microbeads.

During production of the finished product, a palatabilizer for cats was added to the solution for encapsulation by prilling of surfactants to make the product even more attractive for animals.

Addition of the palatabilizer at a dose of 0.5% did not alter the "prilling" conditions or the release profiles.

EXAMPLE 3: CASE OF A VETERINARY ADDITIVE FOR RUMINANTS

In this example we are interested in a hydrophilic active principle for feeding bovines, soluble in thirty seconds in the ruminant's rumen.

The objective is to encapsulate it so that it is released in the bovine rumen gradually in about six to eight hours.

The aim is to encapsulate this active substance in mixtures involving at least two surfactants having different HLB values to obtain a targeted release profile, characterized by the release of about 20% of the active substance administered after one hour, 40% after four hours and 50% after six hours.

The composition adopted comprises:
  Two surfactants: Sorbitan stearate—lipophilic surfactant of HLB 4.7 and ethoxylated sorbitan stearate (20 EO)—hydrophilic surfactant of HLB 15.
  A diluent: hydrogenated palm oil The HLB of the composition is 5.1; the proportions by weight of its constituents are given below for 100% of the weight of said composition:
  Hydrogenated palm oil: 74%
  Sorbitan stearate: 25%
  Ethoxylated sorbitan oleate 20 EO: 1%.

Encapsulation of the active substance is carried out by spraying the molten composition at 70° C. on the active substance in a film-coating turbine, the temperature of which is kept close to 50° C. Spraying is effected with Accucoat® apparatus equipped with a gun of the Airless type.

Dissolution of the active substance is carried out in a dissolution bench according to the European Pharmacopeia. 2.5 g of microcapsules are dispersed in one liter of an aqueous solution at pH 6, maintained at 37° C. with a stirring speed of 100 rev/min. The release of the active substance is monitored by taking regular samples for analysis of said active substance by spectrophotometry at 420 nm.

Figure 4:
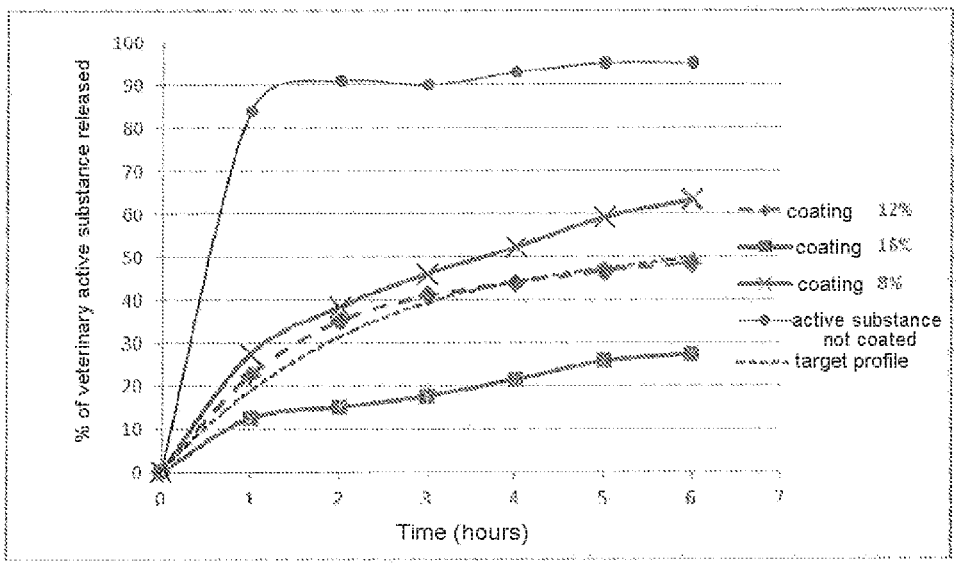

The curves in FIG. 4 show that the targeted release profile can be achieved by encapsulating 88 wt % of active substance in 12% of the composition adopted and that the release profile can be adjusted as a function of the amount of the composition deposited on the active substance: the greater the amount deposited, the slower the dissolution of the active substance.

EXAMPLE 4: EFFECT OF THE HLB OF THE ENCAPSULATING COMPOSITION ON THE RELEASE OF A VETERINARY ADDITIVE FOR RUMINANTS

Different compositions of hydrophilic and lipophilic surfactants diluted in a hydrogenated vegetable oil were studied for encapsulating the veterinary active substance from example 3.

The active substance is for example an amino acid such as choline, urea, vitamins (for example vitamin C), or a mineral salt (of calcium or of iron).

Sorbitan stearate is a lipophilic surfactant with HLB 4.7. Ethoxylated sorbitan oleate with 20 moles of ethylene oxide is a hydrophilic surfactant with HLB 15.

The release kinetics of the active substance was measured in the same conditions as described above in example 3.

The compositions by weight of the fatty phases employed for encapsulating the active substance are given below, for 100% of the weight of the compositions formed.

| Reference | Hydrogenated vegetable oil (%) | Sorbitan stearate (%) | Sorbitan oleate 20 EO (%) | HLB of the composition |
|---|---|---|---|---|
| 9 | 47.5 | 47.5 | 5 | 5.7 |
| 10 | 50 | 50 | 0 | 4.7 |

Figure 5:
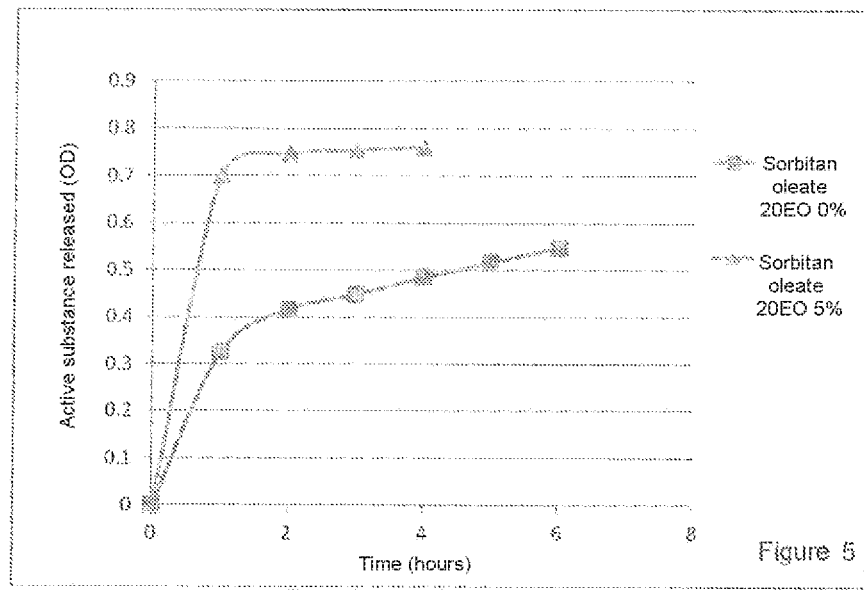

The curves in FIG. 5 show the release kinetics of the active substance determined in the same experimental conditions as those described above. Once again it is found that the rate of release increases with the HLB of the coating composition.

In another series of tests, we formulated capsules comprising, for 100% of their weight, 90 wt % of active substance and 10 wt % of coating, having the following compositions for 100 wt % of said coating.

| Reference | Hydrogenated vegetable oil (%) | Sorbitan stearate (%) | Sorbitan oleate 20 EO (%) | HLB of the composition |
|---|---|---|---|---|
| 11 | 75 | 25 | 0 | 4.7 |
| 12 | 74.3 | 24.7 | 1 | 5.1 |
| 13 | 72.8 | 24.2 | 3 | 5.8 |

Figure 6:
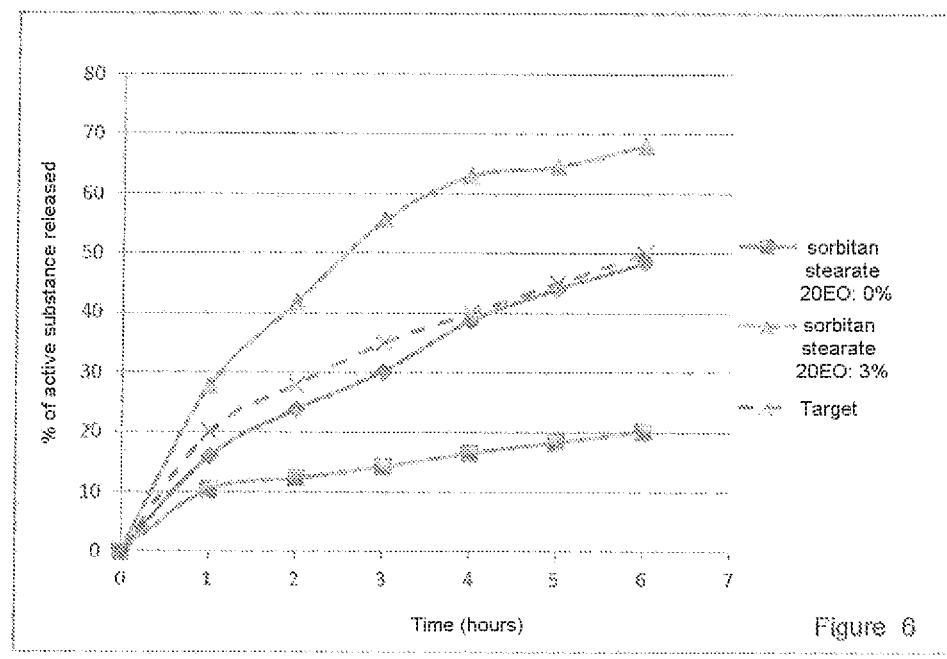

The curves of release of the active substance presented in FIG. 6 show that a targeted profile may be achieved by adjusting the concentration of hydrophilic surfactant to 1% in the coating composition.

EXAMPLE 5: ENTERIC MICROBEADS COMPRISING TWO SURFACTANTS

The objective is to develop a composition that is in the form of microbeads and contains an active pharmaceutical ingredient, diclofenac sodium, that does not dissolve in the stomach at acid pH, but allows release of the active principle in the intestine (for a pH value greater than or equal to 5 and less than or equal to 8).

To achieve this objective, we formulated a composition comprising a combination of two surfactants: a lipophilic surfactant (sorbitan stearate, HLB=4.7) and a surfactant whose HLB value varies as a function of the pH. Stearic acid is lipophilic in an acid environment and hydrophilic in a neutral or basic environment (HLB close to 20).

The waxy mixture (sorbitan stearate/stearic acid) is heated to 85° C. on a water bath. The diclofenac sodium is added while stirring with a deflocculator/Rayneri.

When the mixture is homogeneous, it is put in the prilling machine.

Experimental Protocol:

A liquid formula is obtained at 85° C., which sets at room temperature and has the following composition by weight for 100% of its weight:
21% A sorbitan stearate (Montane™ 60),
49% stearic acid,
30% diclofenac sodium.

The molten formula is put in the tank of a rotating-disk prilling device made by SPRAI.

The operating parameters for formation of the microbeads are as follows:
tank heating temperature: 85° C.,
heating temperature of the feed pipe for the disk: 85° C.,
disk rotary speed: 50 rev/s,
pressure in the tank: 0.6 bar.

In these conditions, spherical microbeads are obtained with a diameter under 500 μm.

The release of the diclofenac is measured in a dissolution bench according to the European Pharmacopeia:
release medium: solution of HCl at pH=1 (750 mL) for two hours then addition of 250 mL of phosphate buffer and then pH adjustment to 6.8 with 5% NaOH solution. Beads left at pH=6.8 for four hours,
150 g of beads placed directly in the dissolution medium,
amount of the release medium per bowl: 1 L,
amount of medium taken each time: 3 mL,
temperature of the release medium: 37° C.

Figure 7:
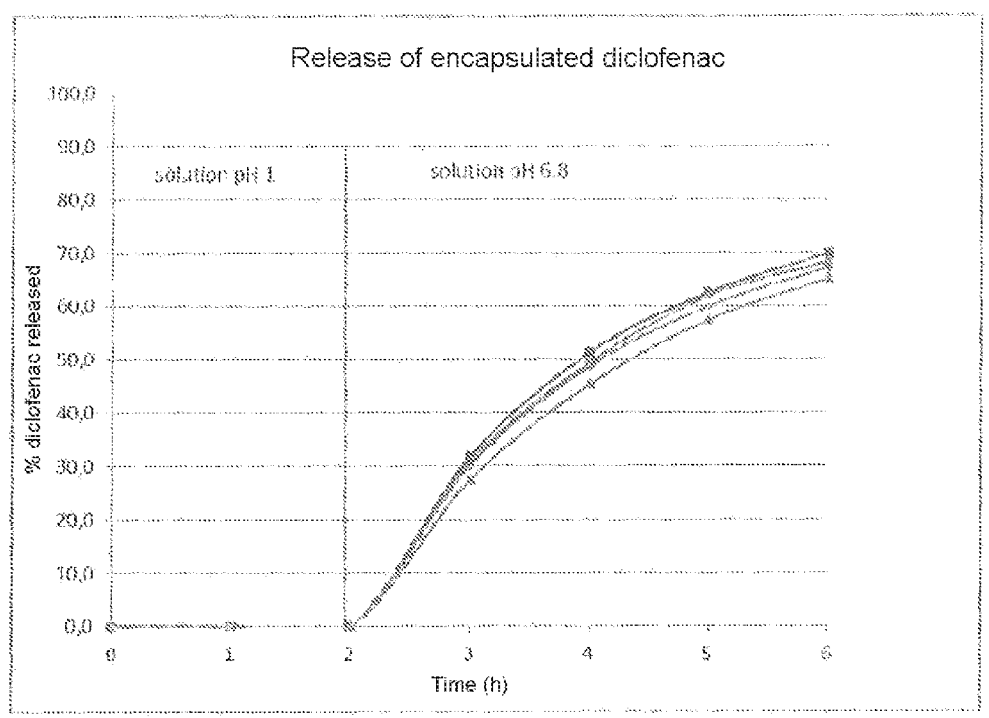

The curve in FIG. 7 shows the release kinetics obtained. It shows that the active substance is not released from the microbeads in acid medium but dissolves quickly as soon as the pH of the dissolution medium is increased to a value of 6.8. The reproducibility of the release kinetics evaluated in four identical tests is good.

The invention claimed is:

1. A water-insoluble composition, of solid appearance at a temperature less than or equal to 20° C., comprising for 100% of its weight:
X1 wt % of at least one lipophilic surfactant having an HLB value, H1, greater than or equal to 1 and below 10;
X2 wt % of at least one hydrophilic surfactant consisting of ethoxylated sorbitan oleate and having an HLB value, H2, of greater than or equal to 14 and less than or equal to 16;
characterized in that its HLB=X1.H1+X2.H2, X1 and X2 varying from 2 to 60, and characterized in that it is free from acrylic polymer and/or succinate acetate.

2. The composition as claimed in claim 1, characterized in that H1 is greater than or equal to 3.4 and less than or equal to 6 and H2 is 15.

3. The composition as claimed in claim 1, characterized in that it comprises from two to five surfactants each having an HLB, Hi, and a proportion by weight Xi such that the HLB value of said composition is equal to Σ Xi.Hi, with i between 2 and 5, xi between 2% and 60% and Σ Xi≤100%.

4. The composition as claimed in claim 1, characterized in that said at least one lipophilic surfactant is selected from
esters of fatty acids and sugars; said fatty acids being selected from stearic, palmitic, ketostearic, arachidic, and behenic acids; said sugars being selected from glucose, sorbitol, mannitose, mannitol, sucrose, mannose, xylitol or xylose;
esters of fatty acids and glycerol, said fatty acids being selected from stearic, palmitic, ketostearic, arachidic, and behenic acids;
ethers of fatty alcohols and sugars, the fatty alcohols being stearic, palmitic, ketostearic, arachidic, and behenic alcohols; said sugars being selected from glucose, xylose, arabinose, mannose, or sucrose;
divalent salts of fatty acids comprising the magnesium, zinc or calcium salts of stearic, palmitic, ketostearic, arachidic, and behenic acids;
fatty alcohols condensed with propylene oxide and/or butylene oxide;
block copolymers of alkoxides (ethylene, propylene, butylene, etc.), rich in propylene oxide or butylene oxide.

5. The composition as claimed in claim 1, characterized in that said at least one lipophilic surfactant is a sorbitan monostearate with an HLB value of 4.7.

6. The composition as claimed in claim 1, characterized in that it further comprises, to 100% of its weight, an amount of additives comprising a perfume, a flavoring, a palatabilizer, a dye, a pigment, or a solid diluent at a temperature less than or equal to 20° C.

7. A controlled-release galenical formulation comprising for 100% of its weight:
   from 20 to 95 wt % of at least one pharmaceutical, food or veterinary active substance; and
   from 5 to 80 wt % of a water-insoluble composition, of solid appearance at a temperature less than or equal to 20° C., comprising for 100% of its weight:
   X1 wt % of at least one lipophilic surfactant having an HLB value, H1, greater than or equal to 1 and below 10;
   X2 wt % of at least one hydrophilic surfactant consisting of ethoxylated sorbitan oleate and having an HLB value, H2, of greater than or equal to 14 and less than or equal to 16;
   characterized in that its HLB=X1.H1+X2.H2, X1 and X2 varying from 2 to 60, and characterized in that it is free from acrylic polymer and/or succinate acetate,
   wherein the water-insoluble composition encapsulates the at least one pharmaceutical, food or veterinary active substance, and
   wherein the controlled-release functionality of the galenical formulation arises from the encapsulation with the water-insoluble composition.

8. The formulation as claimed in claim 7, characterized in that the active substance is selected from the antiulcer drugs, antidiabetic drugs, anticoagulants, antithrombotics, hypolipemic drugs, antiarrhythmic drugs, vasodilators, antiangina drugs, antihypertensives, vasoprotective agents, antibiotics, antifungals, antivirals, anticancer drugs, antiinflammatories, analgesics, antiepileptics, antiparkinsonian drugs, neuroleptics, hypnotics, anxiolytics, psychostimulants, antimigraine drugs, antidepressants, antitussives, antihistamines or antiallergic drugs.

9. The formulation as claimed in claim 8, characterized in that the active substance is selected from the following compounds: metformin, acetylsalicylic acid, pentoxifylline, prazosin, acyclovir, nifedipine, diltiazem, naproxen, ibuprofen, flurbiprofen, ketoprofen, fenoprofen, indomethacin, diclofenac, fentiazac, estradiol valerate, metoprolol, sulpiride, captopril, cimetidine, zidovudine, nicardipine, terfenadine, atenolol, salbutamol, carbamazepine, ranitidine, enalapril, simvastatin, fluoxetine, alprazolam, famotidine, ganciclovir, famciclovir, spironolactone, 5-ASA, quinidine, morphine, pentazocine, paracetamol, omeprazole, metoclopramide and mixtures thereof.

10. The formulation as claimed in claim 7, characterized in that the active substance is selected from a list of nutraceuticals: tonics, antioxidants, iron salts, vitamins, urea, caffeine.

11. The use of a composition as defined in claim 1 for encapsulation of a pharmaceutical, food or veterinary active substance in a controlled-release galenical formulation.

12. The formulation as claimed in claim 7 characterized in that the active substance is hydrophilic.

13. The formulation as claimed in claim 7 characterized in that the active substance is hydrophilic and soluble in a ruminant's rumen in thirty seconds.

14. The formulation as claimed in claim 7 characterized in that said at least one lipophilic surfactant is a sorbitan monostearate with an HLB value of 4.7 and in that the active substance is hydrophilic and soluble in a ruminant's rumen in thirty seconds.

* * * * *